United States Patent [19]
Bedoukian

[11] Patent Number: 4,920,096
[45] Date of Patent: Apr. 24, 1990

[54] METHOD FOR EXTRACTING CEDAR WOOD OIL

[76] Inventor: Paul Z. Bedoukian, 96 Warncke Rd., Wilton, Conn. 06897

[21] Appl. No.: 255,356

[22] Filed: Oct. 6, 1988

[51] Int. Cl.[5] .......................... C11B 9/00; C07C 35/18
[52] U.S. Cl. .......................... 512/5; 512/8; 512/25; 568/826; 568/827
[58] Field of Search .......................... 512/5, 8, 25; 568/817, 568/838, 826, 827

[56] References Cited

U.S. PATENT DOCUMENTS 4,142,997 3/1979 Maurer .......................... 568/817

OTHER PUBLICATIONS

Stork, "J. Amer. Chem. Soc.", vol. 75, p. 3291, (1953).

*Primary Examiner*—Werren B. Lone
*Attorney, Agent, or Firm*—Mattern, Ware, Stoltz & Fressola

[57] ABSTRACT

High quality cedar wood oil is recovered from raw cedar wood with substantially improved efficiency employing the solvent extraction method of this invention. By submerging cedar wood pulp or sawdust in a suitable water insoluble solvent for a predefined time period, a purified cedar wood oil extract is easily attained after filtration of the cedar wood pulp and distillation removal of the solvent. Furthermore, depending upon the end use or operating system, the solvent extraction method of this invention may be conducted as either a batch process or a continuous process.

9 Claims, No Drawings

METHOD FOR EXTRACTING CEDAR WOOD OIL

TECHNICAL FIELD

This invention relates to methods for extracting oil from cedar wood, and more particularly to the removal of cedar wood oil by solvent extraction.

BACKGROUND ART

Cedar wood oil has long been employed for various products, particularly cosmetic products and perfumes. With the ever increasing popularity of these products and the development of new products in these fields, the demand for high quality cedar wood oil continues to climb.

In spite of this increased demand and the large quantity of cedar wood available for use by manufacturers, the production of cedar wood oil has not kept up with the demand and the expense of obtaining the cedar wood oil has not been made more efficient. These drawbacks are principally due to the methods used to remove the cedar wood oil from the base material.

The sole production method being employed in the industry to obtain cedar wood oil from cedar tree pulp is steam distillation. Although various attempts have been made to improve the steam distillation process, the process has remained substantially the same for decades, with its numerous drawbacks and inefficiencies remaining intact.

In particular, the use of steam distillation is extremely expensive due to the requirement that large of quantities of steam must be generated and forced through the cedar wood pulp in order to extract the desired oil therefrom. This removal or distillation process is extremely time consuming with about twenty hours being required to obtain a recovery of about 2% cedar wood oil.

In addition to the high cost for meeting the requirement that steam be continuously forced through the batch of cedar wood pulp, the prior art methods also suffer from the inherent problems encountered by channeling. Typically, the steam develops specific flow paths as the steam is initially forced through the cedar wood pulp, and these flow paths are repeatedly followed by the subsequent steam flow, instead of extending through the entire reservoir of cedar wood pulp. As a result, the process is inefficient in using the expensive steam to extract larger quantities of cedar wood oil since the entire batch is not efficiently processed, unless specific steps are taken to eliminate chaneling.

Furthermore, additional problems typically encountered with steam distillation of cedar wood oil are severe pollution problems whereby caustic or harmful smoke and/or grease are given off to the environment through smoke stacks, even though every effort is made to eliminate these unwanted environmental hazards.

Therefore, it is a principal object of the present invention to provide a process for removing cedar wood oil from the cedar wood pulp in a more efficient, less time consuming method.

Another object of the present invention is to provide a process for removing cedar wood oil from cedar wood pulp having the characteristic features described above which can be easily employed in all process facilities, even facilities presently using steam distillation.

Another object of the present invention is to provide a process for removing cedar wood oil from cedar wood pulp having the characteristic features described above which substantially reduces the manufacturing expense of the final product.

A further object of the present invention is to provide a method for removing cedar wood oil from cedar wood pulp having the characteristic features described above which is capable of providing a higher quality product with substantially less energy costs.

Another object of the present invention is to provide a process for removing cedar wood oil from cedar wood pulp having the characteristic features described above which substantially eliminates all of the pollution problems inherent in steam distillation methods.

Other and more specific objects will in part be obvious and will in part appear hereinafter.

DETAILED DESCRIPTION

The present invention completely eliminates all of the difficulties, expenses and drawbacks presently being encountered with the steam distillation of cedar wood oil by completely deviating from the prior art teachings and employing a completely new recovery process in which the use or need for steam is completely eliminated. It has been found that high quality cedar wood oil is directly removed from the cedar wood pulp by using a solvent extraction process, which is capable of being efficiently operated at room temperature.

By employing the process of the present invention, cedar wood pulp or sawdust is submerged in a preselected solvent and remains in the solvent for a preselected time span, usually about one hour. Then, the remaining sawdust is filtered out of the liquid extract and the solvent is removed, using a conventional distillation process. The remaining purified extract comprises the purified cedar wood oil being sought.

By employing the solvent extraction process of the present invention, greater quantities of cedar wood oil are removed from the cedar wood in a fraction of the time presently required in the prior art steam distillation process. It has also been found that a further advantage achieved by employing the solvent extraction process of this invention is the fact that the resulting cedar wood oil contains a substantially larger quantity of cedrol, the preferred component of cedar wood oil.

In addition, the cedrene content is low using the process of the present invention. This is very desirable since the cedrene by-product has little commercial value or use and is recovered in substantially larger quantities when cedar wood oil is extracted using the prior art steam distillation methods.

In general, it has been found that by employing the solvent extraction process of the present invention, 40% of the resulting cedar wood oil comprises cedrol, while only 28% to 30% of the cedar wood oil recovered using the steam distillation method comprises the more desirable cedrol component. As a result, the solvent extraction process defined herein provides substantial advantages and improvements over the prior art steam extraction process.

An additional advantage attained by employing the solvent extraction process of the present invention is the fact that the cedar wood pulp or sawdust remaining after the solvent extraction can be used for subsequent processing. It has been found that the solvent employed in the solvent extraction process of this invention does not in any way deleteriously affect the cedar wood pulp after the cedar wood oil has been removed. Consequently, the remaining cedar wood pulp or cedar wood raffinate can be subsequently employed for various other commercial processes.

By employing the solvent extraction process of the present invention, the resulting purified extract obtained after the removal of the solvent by distillation comprises an extremely high quality of purified cedar wood oil. By then further fractionally distilling the purified extract, the various alternate cedar wood oil components can be obtained in substantially highly purified forms. In addition, the solvent extraction process of this invention may be conducted as either a batch process or a continuous process.

As previously discussed, one of the principal uses of cedar wood oil is an essential oil in perfumes. In this regard, the cedar wood oil most in demand for use in perfumes is the light-colored cedar wood oil, which is formed principally of cedrol. By employing the process of the present invention, this desirable light colored oil can be easily obtained bY distillation of the purified cedar wood oil extract resulting after the removal of the solvent. In this way, the most desirable by-product of cedar wood is attained directly in a substantially purified form, using a process which is substantially less expensive to operate for the amount of oil obtained when compared to the prior art steam distillation methods.

In carrying out the present invention, any water insoluable solvent having a boiling point below the cedar wood oil components can be employed. Suitable solvents include toluene, benzene, carbon tetrachloride, and methyl isobutyl ketone.

Although virtually any water insoluble solvent can be employed in carrying out the solvent extraction process of the present invention, it has been found that toluene provides a readily available, highly effective solvent. Furthermore, it has been found that the toluene can be removed, substantially in its entirety, from the extract resulting from the processing of the cedar wood pulp or sawdust, thereby further enhancing the purity of the resulting cedar wood oil. In addition, with the toluene removed substantially in its entirety, it can be recycled for further use in carrying out subsequent processing.

In addition, although the entire process can be completed in one hour at room temperature, the processing time can be reduced by warming the cedar wood/toluene batch during processing. Although warming is not required in carrying out the teaching of the present invention, whenever the processing time is of critical importance, such requirements can be met by warming the toluene/cedar wood batch, without reducing the efficacy of the extraction method of the present invention.

EXAMPLES

In order to show the efficacy of the present invention, the liquid extraction method of the present invention was employed in a batch process to obtain the desired cedar wood oil. In this test procedure, 40 kilograms of cedar wood powder or sawdust was employed. To this batch of cedar wood powder, a sufficient quantity of toluene was added, so that the entire amount of cedar wood sawdust was completely covered by the toluene solvent. The toluene and cedar wood sawdust combination was allowed to stand for one hour. Then, the extract was obtained by passing the entire batch through a filter for removal of the cedar wood sawdust.

The extract resulting from this procedure was passed to a conventional distillation unit to remove the toluene from the extract. The resulting purified extract comprised 1800 grams of purified, dark cedar wood oil. This extract was then further processed by using a vacuum distillation unit. This resulted in the production of 960 grams of the most desirable, light-colored cedar wood oil, of which 40% comprised cedrol.

As is apparent from this test result, the recovery rate of the cedrol based upon the amount of cedar wood sawdust initially employed was about 2.4%. Although this alone is a substantial improvement over the results attained using the prior art steam distillation process whereby recovery rates of about 2.0% are typically realized, the process of this invention is clearly a substantial improvement since the improved recovery rate is obtained in one hour, as opposed to the 20 hours required for steam distillation with the high energy expense needed to provide the steam throughout the entire 20 hour time period.

It will thus be seen that the objects set forth above, among those made apparent from the preceding description are efficiently attained and, since certain changes may be made in the above process without departing from the scope of the present invention, it is intended that all matter contained in the above descriptive shall be interpreted as illustrative and not in a limiting sense.

It is also to be understood that the following claims are intended to cover all of the generic and specific features of the present invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described my invention, what I claim as new and desire to secure by Letters Patent is:

1. A method for extracting cedar wood oil from raw cedar wood comprising the steps of:

A. obtaining a batch of raw cedar wood;

B. covering the raw cedar wood with a water insoluble solvent having a boiling point lower than the cedar wood oil components and maintaining the raw cedar wood in this configuration for a predetermined time period;

C. removing the processed cedar wood from the resulting extract; and

D. removing the solvent from the extract to obtain the purified cedar wood oils.

2. The method for extracting cedar wood oil from raw cedar wood as defined in claim 1, wherein said raw cedar wood is further defined as being in a powdered form prior to the application of the solvents.

3. The method for extracting cedar wood oil from raw cedar wood as defined in claim 1, wherein said solvent is further defined as comprising one selected from the group consisting of toluene, benzene, carbon tetrachloride, and methyl isobutyl ketone.

4. The method for extracting cedar wood oil from raw cedar wood as defined in claim 3, wherein the solvent is allowed to remain in contact with the cedar wood for at least one hour.

5. The method of extracting cedar wood oil from raw cedar wood as defined in claim 1, wherein said cedar wood removal step is achieved by filtration.

6. The method defined in claim 1, wherein the solvent is removed from the extract by distillation.

7. The method for extracting cedar wood oil from raw cedar wood as defined in claim 1, comprising the additional step of:

E. distilling the purified cedar wood oils to obtain cedrol.

8. A method for extracting cedar wood oil from cedar wood comprising the steps of:

A. obtaining a batch of powdered cedar wood;

B. covering the entire cedar wood powered batch with toluene;

C. waiting for one hour to allow the processing of the cedar wood powder;

D. filtering the processed cedar wood to obtain the resulting extract;

E. distilling the toluene from the extract to obtain the purified cedar wood oil; and F. fractionally distilling the purified cedar wood oil to obtain the various desired components.

9. The method defined in claim 8, comprising the additional step of:

G. heating the toluene and cedar wood powder mixture to reduce the required processing time.

* * * * *